United States Patent
Kojouri

(10) Patent No.: US 7,604,627 B2
(45) Date of Patent: Oct. 20, 2009

(54) NASOPHARYNGEAL SHEATH FOR NASOGASTRIC INTUBATION

(76) Inventor: Kourosh Kojouri, 5701 Capilano Dr., San Jose, CA (US) 95138

( * ) Notice: Subject to any disclaimer, the term of this patent is extended or adjusted under 35 U.S.C. 154(b) by 8 days.

(21) Appl. No.: 11/431,861

(22) Filed: May 11, 2006

(65) Prior Publication Data

US 2007/0265569 A1 Nov. 15, 2007

(51) Int. Cl.
*A61M 31/00* (2006.01)
(52) U.S. Cl. .................................... 604/516
(58) Field of Classification Search ............. 604/117, 604/164.01, 516, 529, 171, 170.03, 177, 604/172
See application file for complete search history.

(56) References Cited

U.S. PATENT DOCUMENTS

| | | | | |
|---|---|---|---|---|
| 4,166,469 A | * | 9/1979 | Littleford | 607/122 |
| 4,167,939 A | * | 9/1979 | Storz | 600/114 |
| 4,175,564 A | * | 11/1979 | Kwak | 604/171 |
| 4,257,421 A | * | 3/1981 | Beal | 604/170.01 |
| 4,306,562 A | * | 12/1981 | Osborne | 604/523 |
| 4,411,654 A | * | 10/1983 | Boarini et al. | 604/165.04 |
| RE31,855 E | * | 3/1985 | Osborne | 604/161 |
| 4,596,559 A | * | 6/1986 | Fleischhacker | 604/164.05 |
| 4,601,713 A | * | 7/1986 | Fuqua | 604/514 |
| 4,687,470 A | | 8/1987 | Okada | |
| 4,747,827 A | * | 5/1988 | Micek | 604/516 |
| 4,801,294 A | * | 1/1989 | Okada | 604/171 |
| 4,821,715 A | | 4/1989 | Downing | |
| 4,883,468 A | * | 11/1989 | Kousai et al. | 604/164.05 |
| 4,887,997 A | * | 12/1989 | Okada | 604/516 |
| 4,938,746 A | * | 7/1990 | Etheredge et al. | 604/265 |
| 4,983,168 A | * | 1/1991 | Moorehead | 604/161 |
| 4,997,424 A | * | 3/1991 | Little | 604/161 |
| 5,195,978 A | * | 3/1993 | Schiffer | 604/161 |
| 5,239,982 A | * | 8/1993 | Trautheh | 600/117 |
| 5,320,602 A | * | 6/1994 | Karpiel | 604/514 |
| 5,334,167 A | * | 8/1994 | Cocanower | 604/523 |
| 5,391,158 A | | 2/1995 | Peters | |
| 5,664,567 A | | 9/1997 | Linder | |
| 5,690,620 A | * | 11/1997 | Knott | 604/516 |
| 5,692,506 A | | 12/1997 | Linder | |
| 5,700,252 A | * | 12/1997 | Klingenstein | 604/525 |
| 5,800,414 A | * | 9/1998 | Cazal | 604/523 |
| 6,080,141 A | * | 6/2000 | Castro et al. | 604/523 |

(Continued)

OTHER PUBLICATIONS

Alexander, R. et al., "Nasopharyngeal Airway for Guiding Nasogastric Tubes: Not the Best Choice," *Anesth. Analg.*, 1995, 80:1062.

(Continued)

*Primary Examiner*—Kevin C Sirmons
*Assistant Examiner*—Michael J Anderson
(74) *Attorney, Agent, or Firm*—Moore Patents; David Dreyfuss; Cynthia R. Moore

(57) ABSTRACT

This invention discloses a system for safe and non-traumatic insertion of a nasogastric tube, said system comprises of a nasogastric tube and a curved rubber nasopharyngeal sheath, long enough to reach the hypopharynx from the nostrils. Said sheath has two longitudinal tear-off lines over its full length and two ringed handles to apply lateral pull traction. The diameter of both the tube and the sheath are such that the sheath can accommodate the nasogastric tube. This system can also be used in patients who are endotracheally intubated.

7 Claims, 5 Drawing Sheets

U.S. PATENT DOCUMENTS

| | | | |
|---|---|---|---|
| 6,251,135 | B1* | 6/2001 | Stinson et al. ............. 623/1.34 |
| 6,277,108 | B1* | 8/2001 | McBroom et al. ........... 604/529 |
| 6,379,312 | B2* | 4/2002 | O'Toole ..................... 600/529 |
| 6,582,401 | B1* | 6/2003 | Windheuser et al. ... 604/164.05 |
| 7,014,626 | B2* | 3/2006 | Sanderson .................. 604/171 |
| 7,117,039 | B2* | 10/2006 | Manning et al. ............ 607/119 |
| 2004/0099273 | A1* | 5/2004 | Wright et al. .......... 128/207.18 |
| 2005/0182297 | A1* | 8/2005 | Gravenstein et al. ........ 600/139 |
| 2008/0004598 | A1* | 1/2008 | Gilbert ....................... 604/514 |

OTHER PUBLICATIONS

Chen, Y.S. et al, "A Modified Method to Insert a Nasogastric Tube without Kinking in the Nasal Cavity," *Am. J. Emerg. Med.*, 1992, 10:614-6.

Lewis, J.D., "Facilitation of Nasogastric and Nasotracheal Intubation with a Nasopharyngeal Airway," *Am. J. Emerg. Med.*, 1986, 4:426.

Moustakas, N. et al, "Intracranial Placement of Nasogastric Tube: An Unusual Complication," *South. Med. J.*, 1983, 76:816-7.

Patow, C.A. et al, "Nasogastric Tube Perforation of the Nasopharynx," *South. Med. J.*, 1985, 78:1362-5.

Reussner, L.A. et al, "Nasopharyngeal Perforation as a Complication of Nasogastric Intubation," *ENT J.*, 1993, 72:755-7.

Roubenoff, R. et al, "Pneumothorax due to Nasogastric Feeding Tubes. Report of Four Cases, Review of the Literature, and Recommendations for Prevention," *Arch. Int. Med*, 1989, 149:184-8.

Shetty, S. et al, "A Method to Reduce Nasopharyngeal Trauma from Nasogastric Tube Placement," *Anesth. Analg.*, 1994, 78:410-11.

* cited by examiner

NASOPHARYNGEAL SHEATH FOR NASOGASTRIC INTUBATION

CROSS-REFERENCE TO RELATED APPLICATION

Not Applicable.

Statement Regarding Federally Sponsored Research or Development

Not Applicable.

Reference to Sequencelisting, a Table, or a Computer Program Listing Compact Disc Appendix Not Applicable.

BACKGROUND OF THE INVENTION

1—Field of Invention

The present invention is in the field of medicine, particularly in relation to nasogastric catheter placement.

2—Description of the Prior Art

Nasogastric intubation has been practiced for a very long time. This has been always a difficult and uncomfortable procedure. The tip of the nasogastric tube frequently causes injury to the nasal passage mucosa. This is because of the anatomical configuration of human nasal passage which includes a sharp curve at the nasopharynx. There are various types of nasogastric tubes from simple ones to the recently introduced sump drain nasogastric tubes. A problem that is always present with these tubes is their rigidity vs. maneuverability. If the catheter is rigid enough to be able to be maneuvered and pushed through the nasopharynx and hypopharynx into the esophagus, it may well injure the mucosa by it's tip, and if it is made of very soft material it may not be easily maneuvered and needs a rigid stylet to assist during insertion, but these will collapse their internal lumen if connected to suction because their wall is so soft and pliable and are suitable only for purpose of feeding not for suctioning. Examples of the first type of tubes are the currently used nasogastric suction catheters and examples of the second group include the current enteric feeding tubes.

In order to overcome these shortcomings, several inventions have been disclosed before.

For the rigid catheters a lumen seeking nasogastric tube with a flexible tip was disclosed by Klingenstein (U.S. Pat. No. 5,700,252, December, 1997). Another prior art is a stylet to help the tube negotiating the nasopharyngeal curve (Micek, U.S. Pat. No. 4,747,827, May, 1988).

For the softer tubes disclosures includes multiple type of conduit tubes to push the feeding tube through the nasopharynx or hypopharynx all the way to the stomach and then removing the conduit (Okada, U.S. Pat. No. 4,887,997, December 1989) or stylets to temporarily stiffen the tube (Etheredge, U.S. Pat. No. 4,938,746, March 1988; Beal, U.S. Pat. No. 4,257,421, March 1981). The conduit proposed by Okada proposed a conduit that it is to be inserted all the way to the stomach and then after placement of the nasogastric tube that conduit is removed via a special separator. This is different to the current disclosed nasopharyngeal sheath because the main difficulty and concern for mucosal injury still exists with the Okada's conduit. It is mainly targeted for placing the very soft feeding tubes, which are not suitable for nasogastric suctioning. Kwak (U.S. Pat. No. 4,175,564) proposes to insert the nasogastric tube through the nose and pull it through the mouth then a guide to be inserted through the mouth into the esophagus and the nasogastric tube will pass through it into the esophagus. This technique still requires passing the nasogastric tube through the nasopharyngeal airway with potential for causing injury. There are also innovative approaches including swallowing an absorbable string to guide the catheter during insertion (Peters, U.S. Pat. No. 201,556, February 1994).

The shape of human nasopharynx is such that it has a sharp curve at its passage to pharynx and subsequently hypopharynx. Passing tubes and catheters often causes injury to the mucosa and bleeding of the posterior wall of the nasopharynx. Tubes that have inherent curve on the other hand can easily pass through this curve; examples are the current nasopharyngeal airway catheters. The same problem exits even when a patient is endotracheally intubated. Placing a nasogastric tube can still be very traumatic. Also, in patients who have problems with their coagulation, conventional nasopharyngeal intubation can potentially cause significant bleeding because of the mucosal injury.

It is to be said that the disclosed nasopharyngeal sheath is different comparing to the current commercially simple nasopharyngeal airway catheters or their various modifications like the ones described by Downing or Linder among others (U.S. Pat. No. 4,821,715 which issued on Apr. 18, 1989 to Michael V. Downing, U.S. Pat. No. 5,664,567 which issued on Sep. 9, 1997 to Gerald S. Linder and in U.S. Pat. No. 5,692,506 which issued on Dec. 2, 1997 also to Gerald S. Linder). The scopes of function of the two are completely different. The curve of the nasopharyngeal airway catheter is such that it places the tip of the catheter as close to the tracheal opening as possible and all the modifications mentioned above aim to better deliver oxygen to the patient, while the disclosed sheath has a wider curve to be able to point more posteriorly towards the esophagus rather than the trachea which is located more anteriorly. Also none of the current nasopharyngeal airways have the tear-off mechanism or the pulling rings.

The disclosed invention uses a curved rubber tube to secure a safe pathway for the nasogastric tube into the hypopharynx. Once there, the tip of the rubber sheath positions the nasogastric tube tip above the esophageal aperture, therefore the catheter can be easily pushed into the esophagus. For further understanding and appreciation of the invention and its advantages reference is made to the Drawings and Detailed Description below.

BRIEF SUMMARY OF THE INVENTION

This invention provides a comfortable and safe way to insert any nasogastric tube. According to the present invention a curved rubber sheath is first inserted into the nasopharynx all the way to the hypopharynx. The natural curve of this tube corresponds to the natural curve of these areas in human body. The beveled and round edge as well as its rubber material all minimizes the risk of mucosal injury. By bending the patient's head forward the curved sheath tip will position itself right above the esophageal opening. Then through this sheath a nasogastric catheter can easily slide into the esophagus with no trauma to the mucosa, and then the sheath is retracted outside and torn apart. As the last step the nasogastric catheter will be fixed to the nose.

The objective of this invention is to provide a safe and less traumatic method and means for introducing nasogastric catheters.

Another objective of this invention is to improve the success rate of esophageal intubation vs. accidental tracheal intubation.

Another objective of this invention is to prevent injury and bleeding in patients especially those with coagulation problems.

Yet another objective of this invention is to provide a less traumatic nasogastric intubation technique for patients who are under general anesthesia and have endotracheal intubation and need to have a nasogastric tube as well.

Through these two goals the ultimate objective of this invention is to improve patient's comfort and tolerance during a difficult procedure.

DETAILED DESCRIPTION OF THE INVENTION

Figure 1:
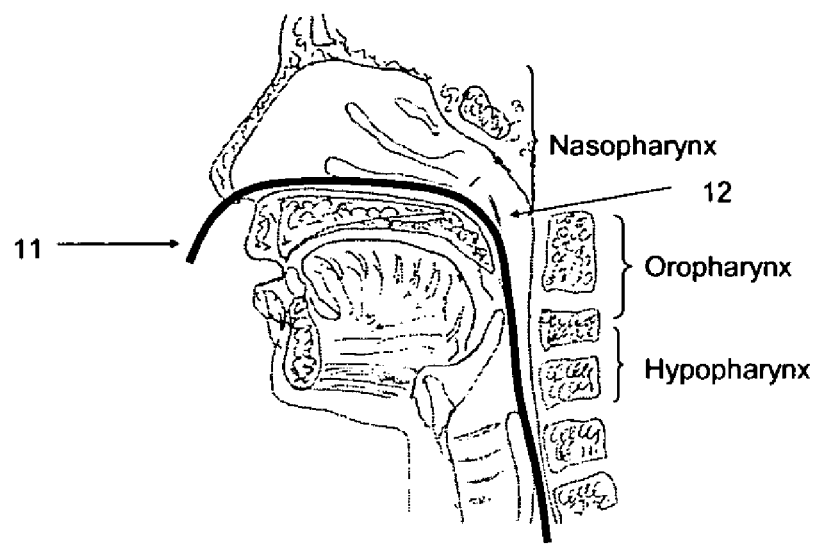
FIGS. 1 and 2 are views of the human aero-digestive tract and the usual path of a nasopharyngeal tube.
Figure 2:
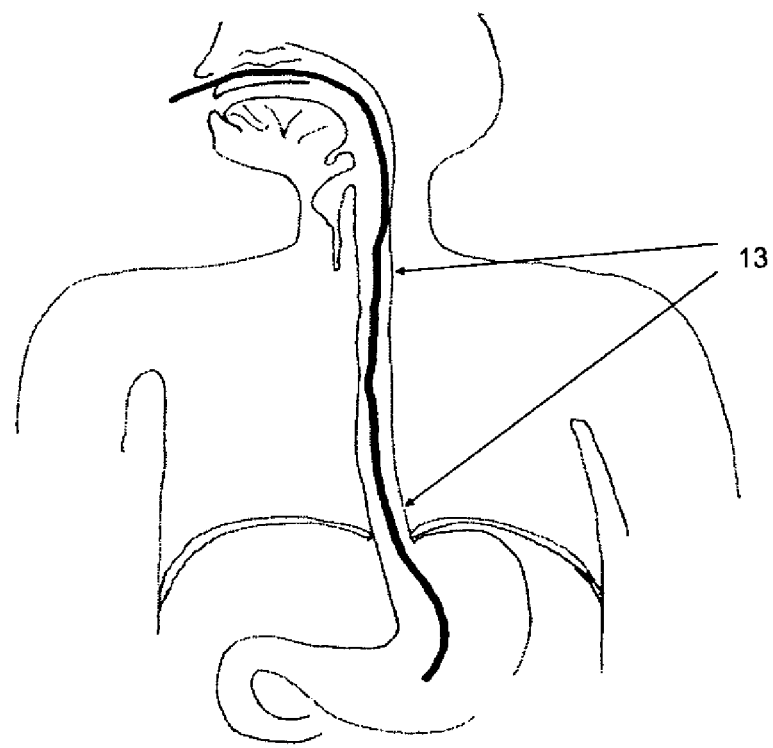

The anatomy of human nasopharynx and oropharynx is shown in FIGS. 1 and 2. The bold line (11) indicates the path of a nasogastric tube. As it is demonstrated a straight tube placed in the nose will hit the posterior nasopharyngeal wall (12) before it is pushed down towards the oropharynx. After entering the esophagus the path of a nasogastric tube to the stomach is almost a straight line (13). The conventional nasogastric intubation technique involves negotiating the curve of the nasopharynx. The injury usually occurs in the nasal mucosa or more severely at the nasopharynx.

Figure 3:
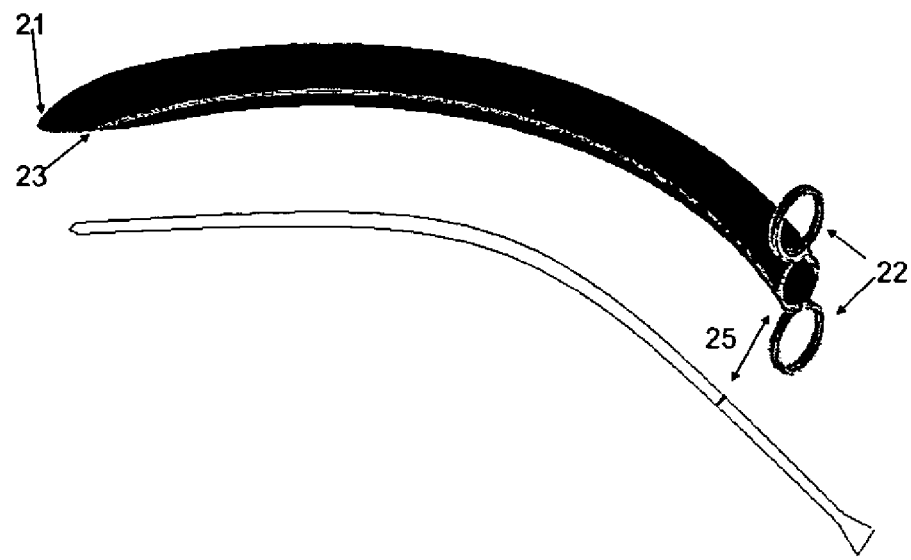
FIGS. 3, 4, 5, and 9 are the nasopharyngeal sheath from different views.
Figure 4:
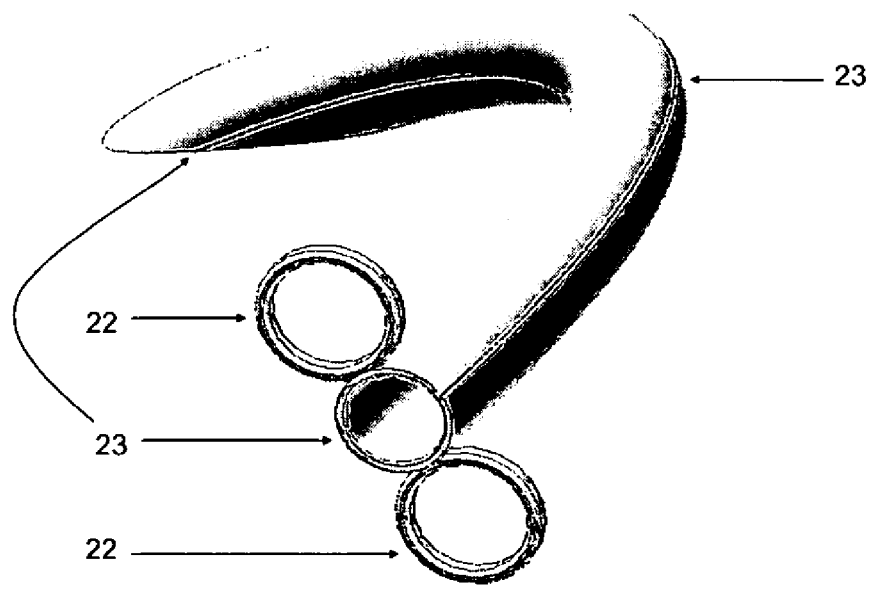
Figure 5:
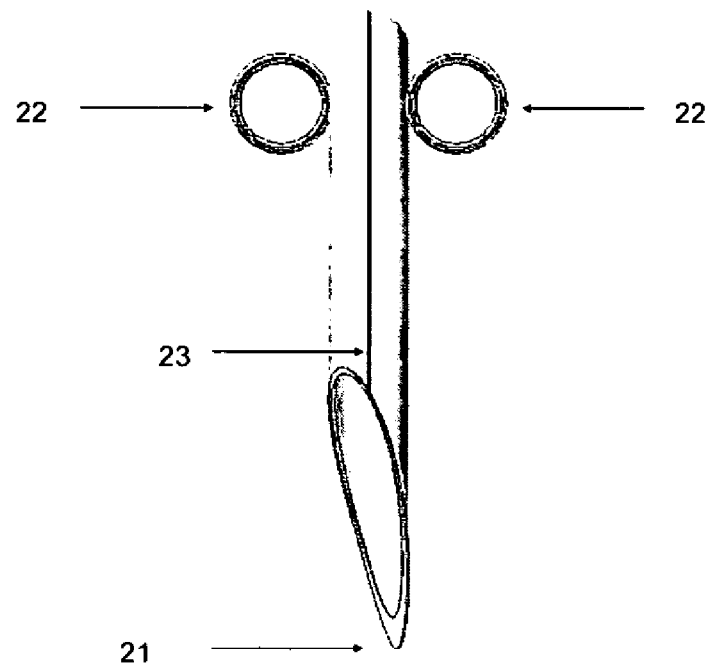

Referring to FIGS. 3, 4, and 5, the nasopharyngeal sheath has a curve to correspond to the natural curve of the human upper aero-digestive tract. It is made of medically approved rubber or latex. This material is flexible enough to cause minimal damage to the surrounding mucosa. Also by using the ordinary medical lubricators the nasogastric tube can slide through them with minimal friction. Its distal tip (21) is rounded and beveled to facilitate its passage through the nasal mucosa. There are two tear-off lines that extend through the entire length of the catheter at 12 and 6 o'clock. These are slits in the body of the nasopharyngeal sheath that extend from its external surface to just short of its internal lumen. Once the rings are pulled apart, the sheath will rip through the two lines. There are two rings (22) at its proximal end to facilitate its tearing through the tear-off lines (23) at the end of the procedure. The rings are attached at the 3 and 9 o'clock positions and are large enough to be easily grabbed and pulled apart. The nasogastric tube has markings (25) on its body to indicate when the tip of the tube is at the distal end of the nasopharyngeal sheath.

The sheath has a thick wall about 1-2 millimeters (24), so that although flexible, but its lumen does not completely collapse during passage through the nasal airway. The length of the sheath should be long enough to extend from the nares to the hypopharynx. It should be supplied in different lengths for different patient populations. The internal lumen also may vary. The usual size of nasogastric tubes is from 8 French to 18 French. Therefore the in internal lumen of the nasopharyngeal sheath should be manufactured in different sizes to be able to accommodate the corresponding nasogastric tube while avoiding an unnecessary large sheath to reduce patients' discomfort. One easy solution would be to supply the nasopharyngeal sheath and the corresponding nasogastric tube in one kit.

Figure 6:
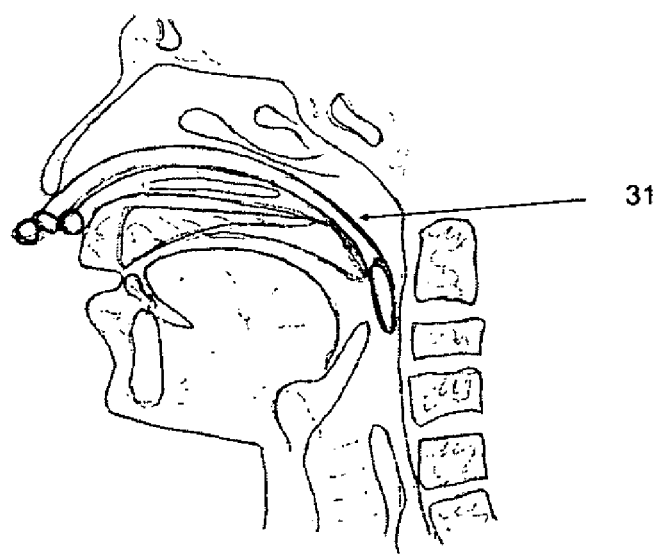
FIGS. 6, 7 and 8 illustrate the technique of nasogastric intubation using the nasopharyngeal sheath.
Figure 7:
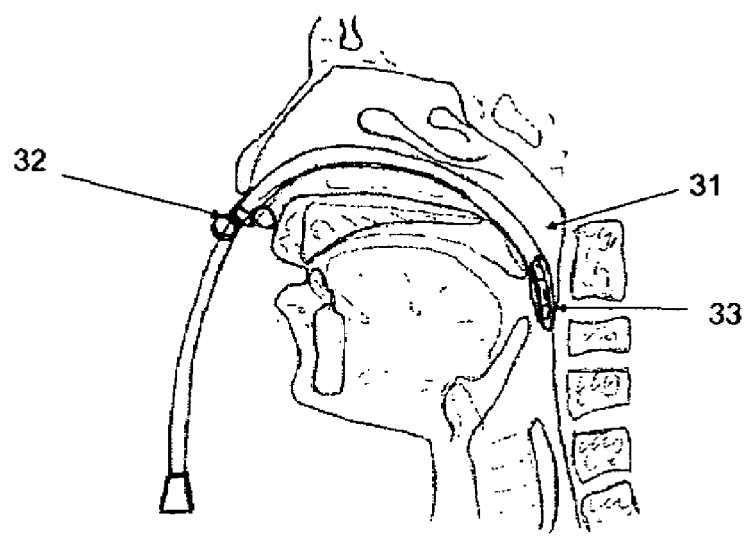
Figure 8:
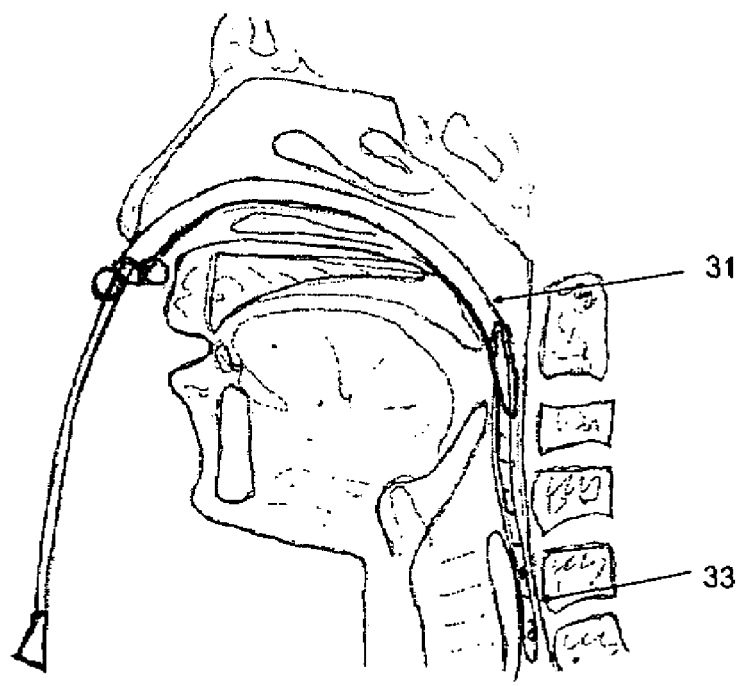

The technique of placement is depicted in FIGS. 6, 7 and 8. This includes placing the lubricated nasopharyngeal sheath initially (31) through the nose all the way to the hypopharynx. The curve of the tube will make this part more tolerable and less traumatic, and then the lubricated nasogastric tube is placed through the sheath. The nasogastric tube is passed through the sheath all the way to the marking (32). This protects the mucosa from injury or irritation and reduces patient's discomfort. The mark corresponds to the point the nasogastric tube tip (33) is right at the proximal end of the sheath as is depicted in FIG. 7.

The patient is instructed to swallow a few sips of water, this further causes the glottis to close the tracheal opening and stimulates the pharyngeal muscle contractions, and then the nasogastric tube can easily be passed into the esophagus and subsequently from there to the stomach is almost a straight route. This is demonstrated in FIG. 8. Bending the head also helps to bring the beveled end of the tube with the posterior pharyngeal wall and places the tip of the nasogastric tube above the esophageal aperture.

Figure 9:
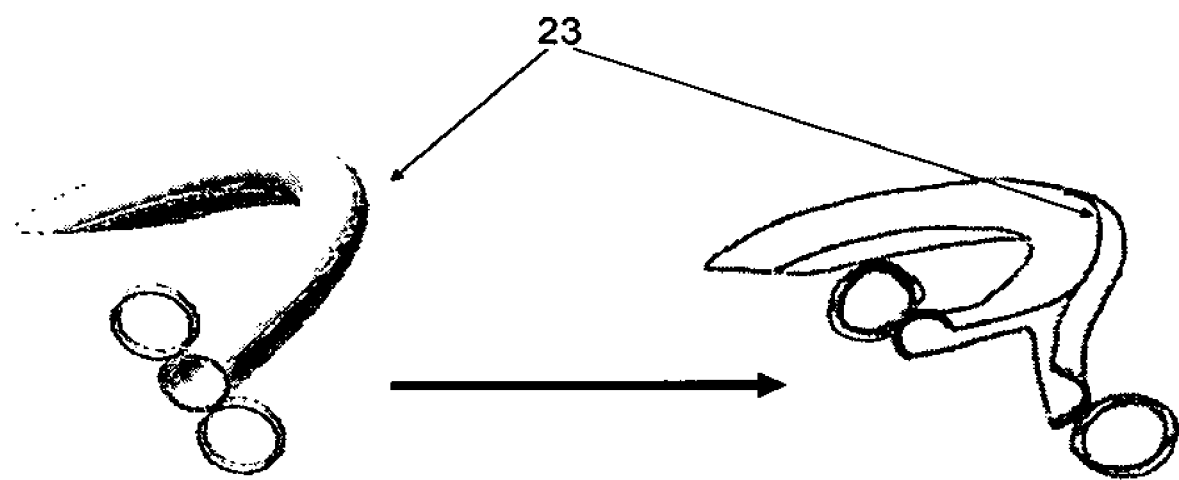

Once the nasogastric tube is in final position, the nasopharyngeal sheath is pulled back out of patient's body and is torn apart through the tear-off lines as it is depicted in FIG. 9. The nasogastric tube is then fixed to the patient's nose. It should be mentioned that in patients who are endotracheally intubated moving the head or swallowing water cannot happen, yet the curve of the nasopharyngeal sheath will facilitate the nasogastric tube placement. Also although in these drawings the nasogastric tube has been illustrated as a simple tubular structure, the current invention can also use the more recently introduced sump suction catheters or the feeding tubes. It is also to be noted that the nasopharyngeal sheath as well as the nasogastric catheter can be manufactured in different matching diameters and lengths so that they can be used a wide range of patient population.

What is claimed is:

1. A method for inserting a nasogastric tube, comprising:
   a. inserting the distal beveled end of a lubricated curved tube, into a patient's nostril,
   b. advancing said distal beveled end of said lubricated curved tube to the hypopharynx,
   c. inserting a nasogastric tube into said lubricated curved tube and advancing said nasogastric tube until the tip of said nasogastric tube is at said distal beveled end of said lubricated curved tube,
   d. optionally, bending said patient's head forward so that said distal beveled end of said lubricated curved tube is positioned just above the esophageal aperture,
   e. advancing said nasogastric tube through the esophagus and then to the desired internal point,
   f. holding said nasogastric tube in place at the nostril and pulling said curved tube back out of said patient's nose,
   g. tearing said lubricated curved tube apart along tear-off lines, and
   h. fixing said nasogastric tube to said patient's nose.

2. The method of claim 1, wherein said nasogastric tube has a mark that is located at a point equidistant from its tip as the length of said curved tube to facilitate step c.

3. A nasopharyngeal sheath for insertion of a nasogastric tube comprising a curved tube, and sufficiently long to reach to the hypopharynx from the nose, wherein said curved tube comprises two rings at the proximal end which prevent insertion beyond the hypopharynx, wherein said curved tube can be retrieved after placement of said nasogastric tube by retracting and tearing apart said curved tube, wherein said curved tube has a curve corresponding to the natural curve of the nasopharynx, and wherein said curve and the length of said curved tube are designed to position the distal end of said curved tube in the hypopharynx above the esophageal aperture.

4. The method of claim 1, wherein said tearing is facilitated by two rings at the proximal end of said curved tube.

5. A method for inserting a nasogastric tube with reduced trauma and discomfort to a patient comprising:
   a. inserting into a patient's nostril a lubricated nasopharyngeal sheath comprising a lubricated curved tube, having a beveled and rounded tip at the distal end and two rings at its proximal end and tear off lines that extend through the entire length of the sheath, wherein the length of said sheath is sufficient to extend from the nares to the hypopharynx, and said rings prevent the sheath from advancing further than the hypopharynx above the esophageal opening,
   b. inserting a lubricated nasogastric tube into said nasopharyngeal sheath and advancing the nasogastric tube until the tip of said nasogastric tube is at the distal end of said lubricated curved tube,
   c. advancing said nasogastric tube through the esophagus and then to the desired internal point,
   d. holding the nasogastric tube in place at the patient's nostril and pulling said lubricated curved tube back out of the patient's body, and
   e. grabbing the two rings and tearing apart said lubricated curved tube along the tear-off lines over the nasogastric tube.

6. The method of claim 5, further comprising after step b., bending the patient's head forward so that the distal end of said curved tube is positioned just above the esophageal aperture.

7. The method of claim 5, further comprising after step b., instructing the patient to swallow.

* * * * *